United States Patent
Shah et al.

(10) Patent No.: US 12,048,915 B2
(45) Date of Patent: Jul. 30, 2024

(54) METHOD FOR MANUFACTURING A SUPPORTED TANTALUM CATALYST

(71) Applicant: Ecovyst Catalyst Technologies LLC, Malvern, PA (US)

(72) Inventors: Parag Rasiklal Shah, Lafayette Hill, PA (US); Yatao Rachel Hu, Malvern, PA (US)

(73) Assignee: ECOVYST CATALYST TECHNOLOGIES LLC, Malvern, PA (US)

( * ) Notice: Subject to any disclaimer, the term of this patent is extended or adjusted under 35 U.S.C. 154(b) by 0 days.

(21) Appl. No.: 17/587,723

(22) Filed: Jan. 28, 2022

(65) Prior Publication Data

US 2022/0241755 A1 Aug. 4, 2022

Related U.S. Application Data (60) Provisional application No. 63/143,484, filed on Jan. 29, 2021.

(51) Int. Cl.
| | | |
|---|---|---|
| *B01J 23/20* | (2006.01) | |
| *B01J 21/08* | (2006.01) | |
| *B01J 35/30* | (2024.01) | |
| *B01J 35/40* | (2024.01) | |
| *B01J 35/61* | (2024.01) | |
| *B01J 35/63* | (2024.01) | |

(Continued)

(52) U.S. Cl.
CPC .............. *B01J 23/20* (2013.01); *B01J 21/08* (2013.01); *B01J 35/397* (2024.01); *B01J 35/40* (2024.01);

(Continued)

(58) Field of Classification Search
CPC . B01J 23/20; B01J 21/08; B01J 35/008; B01J 35/023; B01J 35/1019;

(Continued)

(56) References Cited

U.S. PATENT DOCUMENTS 2,524,848 A * 10/1950 Stahly ..................... C07C 1/207
585/607
4,791,092 A * 12/1988 Wachs ..................... B01J 23/22
502/353

(Continued)

FOREIGN PATENT DOCUMENTS

| CN | 112295556 A | * | 2/2021 | .............. B01J 23/20 |
| JP | 2014210755 A | * | 11/2014 | .............. C07C 1/207 |
| WO | WO-2013024295 A1 | * | 2/2013 | ........... C03C 17/245 |

OTHER PUBLICATIONS

Written Opinion for PCT/US2022/014332. (Year: 2021).*

*Primary Examiner* — Patricia L. Hailey
(74) *Attorney, Agent, or Firm* — Finnegan, Henderson, Farabow, Garrett & Dunner, LLP (57) ABSTRACT

A method for making a supported tantalum oxide catalyst precursor or catalyst with controlled Ta distribution and the resulting supported Ta catalyst. In an embodiment, the method comprises selecting a Ta-precursor with appropriate reactivity with the surface hydroxyls of the solid oxide support material to give a desired Ta distribution in the catalyst precursor or catalyst. In an embodiment the method comprises controlling the number of surface hydroxyls available on the support material to react with the Ta-precursor by thermal methods, such as calcination, to achieve the desired Ta distribution.

22 Claims, 6 Drawing Sheets

(51) Int. Cl.
  *B01J 37/02* (2006.01)
  *B01J 37/04* (2006.01)
  *B01J 37/08* (2006.01)
  *C07C 1/24* (2006.01)
(52) U.S. Cl.
  CPC ........... *B01J 35/615* (2024.01); *B01J 35/635* (2024.01); *B01J 35/638* (2024.01); *B01J 37/0207* (2013.01); *B01J 37/04* (2013.01); *B01J 37/082* (2013.01); *C07C 1/24* (2013.01); *C07C 2521/08* (2013.01); *C07C 2523/20* (2013.01)
(58) Field of Classification Search
  CPC .......... B01J 35/1042; B01J 35/1047; B01J 37/0207; B01J 37/04; B01J 37/082; C07C 1/24; C07C 2521/08; C07C 2523/20

USPC ........................................................ 502/353
See application file for complete search history.

(56) References Cited

U.S. PATENT DOCUMENTS

| | | | |
|---|---|---|---|
| 5,227,482 A * | 7/1993 | Ushikubo | B01J 23/20 540/464 |
| 2010/0209804 A1* | 8/2010 | Shin | H01M 4/9083 429/488 |
| 2016/0082417 A1* | 3/2016 | Lewandowski | C07C 1/20 585/607 |
| 2018/0044199 A1* | 2/2018 | Driessche | C30B 29/30 |
| 2018/0200696 A1* | 7/2018 | Cadran | B01J 35/1061 |
| 2018/0208522 A1* | 7/2018 | Cadran | C07C 1/20 |

* cited by examiner

Sample A:

FIG. 5A

Sample B:

METHOD FOR MANUFACTURING A SUPPORTED TANTALUM CATALYST

This application claims priority to U.S. Provisional Patent Application No. 63/143,484, filed Jan. 29, 2021, which is hereby incorporated by reference in its entirety.

TECHNICAL FIELD

The present disclosure generally relates to methods to make a supported tantalum oxide catalyst precursor and catalyst with controlled tantalum (Ta) distributions. The present disclosure also relates to a supported tantalum oxide catalyst precursor and catalyst with a controlled Ta distribution, such as one having a uniform Ta distribution, especially at Ta loadings substantially below the surface hydroxyl saturation levels, made by the disclosed methods.

BACKGROUND

Supported metal oxides are a class of heterogeneous catalysts that include one or more metal oxide species loaded and bonded to the surface of a support material, such as silica ($SiO_2$), alumina ($Al_2O_3$), titania ($TiO_2$), zirconia ($ZrO_2$), magnesium oxide (MgO) and mixtures therefore. Examples of commonly used metal oxides include groups III-VII metal oxides because they are able to form many different catalysts that are used to synthesize a variety of chemicals. For example, supported tantalum oxide catalysts have been found to catalyze many industrially relevant chemical reactions including the production of 1,3-butadiene from ethanol and the decomposition of methyl t-butyl ether to isobutene and methanol.

The process of producing butadiene from ethanol using supported tantalum oxide catalyst is known to have a variety of limitations, including the production of a wide variety of unwanted by-products. Ta dispersion at an atomic level is known to affect the selectivity and activity of the catalyst. Controlling Ta distribution within a catalyst particle is one of the important factors that influence Ta dispersion in the catalyst. Therefore, for the production of 1,3-butadiene from ethanol using a supported tantalum oxide catalyst, both the Ta loading and the Ta distribution are critical to the performance of the catalyst.

Supported tantalum oxide catalyst made using known Ta-precursors have inherent limitations. For example, the desired Ta distribution within catalyst particles, particularly when the particles are of substantial size for use in packed-bed processes, may not be achieved by using known Ta-precursors. The disclosure herein provides methods for controlling Ta distribution thereby improving selectivity and activity of the resulting catalyst.

The supported tantalum oxide catalyst precursor and catalyst and methods of making described herein are directed to overcoming one or more of the problems set forth above and/or other problems of the prior art.

SUMMARY

There is disclosed a method for making a supported tantalum oxide catalyst precursor with controlled Ta distribution, the method comprising: providing solid oxide or mixed oxide support particles having a surface hydroxyl concentration; selecting a Ta-precursor material having a reactivity appropriate to provide a desired Ta distribution; contacting the solid oxide or mixed oxide particles with the Ta-precursor material mixed with an organic solvent to form Ta-impregnated particles; optionally washing the Ta-impregnated particles to remove unreacted Ta-precursors; recovering the Ta-impregnated particles by removing the solvent to form a catalyst precursor. In one embodiment, the disclosed method may further include a step of calcining the catalyst precursor to form a supported tantalum oxide catalyst comprising a desired Ta distribution.

In one embodiment, the preparation method for making a supported metal oxide catalyst, comprises adding an organic solution containing the active metal precursor (e.g. Ta-ethoxide for Ta) with solvent to the solid oxide support (e.g. silica) via incipient wetness impregnation or slurry reaction and recovering the Ta-impregnated catalyst precursor particles by removing the solvent. The impregnated Ta-precursor in the catalyst precursor is then decomposed (e.g. via heat treatment) to give a dispersed supported metal oxide catalyst. The support can be a solid oxide or mixed oxide support, such as silica ($SiO_2$), alumina ($Al_2O_3$), titania ($TiO_2$), zirconia ($ZrO_2$), hafnium oxide ($HfO_2$), magnesium oxide (MgO) or mixtures thereof. For supported tantalum oxide catalysts, the well-dispersed Ta typically exhibits an oxidation state of +5.

In another embodiment, there is disclosed a method for making a supported tantalum oxide catalyst precursor or catalyst particle having a uniform distribution of Ta therein by controlling the reactivity of the Ta-precursor, e.g., selecting a precursor that is less reactive or performing at least one in-situ treatment to make the precursor less reactive. For example, in one embodiment, there is described a method of stabilizing a Ta-precursor by complexing the Ta-precursor with at least one chemical to slow down the reaction between the Ta compound and the surface hydroxyls on the support. In this embodiment, controlling the reaction rate comprises controlling the reaction rate between the Ta-precursor with the surface hydroxyls on the solid oxide or mixed oxide support to make it approximate to or slower than the mass transfer rate of the precursor towards the center of the particle. In yet another embodiment the choice of solvent may also influence the rate of reaction of the Ta-precursor with the surface hydroxyls.

In an embodiment, there is described a method for making a supported tantalum oxide catalyst precursor particle having controlled distribution of Ta by tuning or manipulating the molar ratio of Ta-precursor to the surface hydroxyls available to react with the precursor (i.e. Ta:OH ratio). This can be achieved by controlling the number of hydroxyl groups in the support prior to reaction with a Ta-precursor in at least one way, such as thermal treatment, e.g. calcination.

In this embodiment there is described a method that includes a calcination step to reduce the hydroxyl concentration on the support material, and thereby increasing the Ta:OH ratio used in the recipe. In one embodiment, this can be achieved by thermally treating, such as calcining, the oxide or mixed oxide support prior to reaction with a Ta-precursor.

There is also disclosed a supported tantalum oxide catalyst precursor or catalyst with controlled Ta distribution made by the method described herein. In one embodiment, the supported tantalum oxide catalyst precursor or catalyst particles have an egg-shell distribution of Ta, as defined herein. In another embodiment, the supported tantalum oxide catalyst precursor or catalyst particles have a uniform distribution of Ta throughout the particle, as defined herein. For example, in an embodiment, there is disclosed a supported tantalum oxide catalyst precursor and catalyst with a controlled Ta distribution, made by a method described herein.

In another embodiment, there is disclosed a method for producing butadiene from ethanol. This method of use comprises contacting ethanol with a supported tantalum oxide catalyst made by a method described herein.

BRIEF DESCRIPTION OF THE DRAWINGS

The accompanying figures are incorporated in and constitute a part of this specification.

DETAILED DESCRIPTION

Definitions

The term "composition" is meant to describe a catalyst precursor, as well as the resulting catalyst.

The phrase "controlled distribution of Ta" is meant to convey that the desired Ta distribution in a catalyst precursor or catalyst particle is purposely obtained.

The phrase "uniform distribution of Ta throughout the particle," means that Ta concentration level at any one point along an exposed diameter of a particle does not vary by more than 20% from the average Ta concentration along the diameter, excluding data points within 5% of each end of the diameter.

The term, "egg-shell distribution" means that most of the Ta is concentrated towards the surface of the particles, with little or no Ta present towards the center of the particles. For example, in an egg-shell distribution Ta concentration levels along an exposed diameter of a particle which generally peak near the ends of the diameter and flatten towards the middle and specifically the peak Ta concentration within the outer 20% of the bead being at least 1.5 times higher than the average Ta concentration, and the Ta concentration in the center of the bead is less than 50% of the average Ta concentration of the bead.

The term "intermediate distribution" includes all types of Ta distributions other than uniform and eggshell described herein.

The term "tantalum oxide" means any oxide of tantalum including but not limited to tantalum pentoxide which has the chemical formula $Ta_2O_5$.

The phrase "recovering the Ta-impregnated particles", involves separating the formed particles from the organic solvent by the described means. This may involve draining the organic solvent from the formed particles and then drying the formed particles in the case of slurry reaction, or just drying the formed particles in the case of incipient impregnation. As previously indicated, the disclosed method may include an optional step of washing the Ta-impregnated particles to remove unreacted Ta-precursors prior to the recovery step. In one embodiment, the Ta-impregnated particles after recovery may be further calcined to decompose the Ta-precursor to convert it to a tantalum oxide.

The solid oxide support, such as silica ($SiO_2$), alumina ($Al_2O_3$), titania ($TiO_2$), zirconia ($ZrO_2$), hafnium oxide ($HfO_2$), magnesium oxide (MgO), and mixtures thereof. As used herein, a support comprising mixed oxide particles encompasses an oxide support that contains cations of more than one chemical element, each being present in an amount above trace amounts or the level of impurities, such as at least 0.1% by weight, above 0.5% by weight, or even above 1% by weight. In one embodiment the solid oxide or mixed oxide support can have a moisture content of less than 10 wt %, such as less than 5 wt %, or even less than 2 wt % water. In an embodiment, the solid oxide support has less than 0.5% water by weight, such as less than 0.1% water by weight. If a drying step is necessary to achieve these levels of moisture, it can be accomplished by drying at a temperature of about 120-200° C. for a time up to 12 hours.

Analysis Methods

Ta distribution: To measure Ta-distribution as described herein, a particle was embedded in an epoxy resin, cut into hemispheres, and the face of the hemisphere embedded was polished. The Ta-distribution through the particle along a diameter of the polished hemisphere face was then measured using the standardless EDS spectrum analysis using Bruker Nano QUANTAX 200 system, with the Bruker Nano XFlash 6130 detector attached to a Hitachi SU6600 scanning electron microscope. Ta content was calculated based on the P/B-ZAF method on the Ta L lines.

Ta levels: The levels of Ta in the catalyst compositions were measured by Inductively Coupled Plasma ("ICP") Spectroscopy using a Perkin Elmer Optima 8300 ICP-OES spectrometer. Results are reported on dried weight basis of the catalyst calcined at 500 to 550° C.

Surface Area and Pore Volume: The surface area and pore volume were measured by Nitrogen Porosimetry using an Autosorb-6 Testing Unit from Quantachrome Corporation (now Anton Paar GmbH). Samples were first degassed at 350° C. for at least 4 hours on the Autosorb-6 Degassing Unit. A multipoint surface area is calculated using the BET theory taking data points in the $P/P_0$ range 0.05 to 0.30. A pore volume measurement is recorded at $P/P_0$ of 0.984 on the desorption leg. Average pore diameter is calculated using the following equation assuming cylindrical pores.

$$\text{Average pore diameter}(\text{Å}) = \frac{40000 \times PV\left(\frac{cc}{g}\right)}{SA\left(\frac{m^2}{g}\right)}$$

Particle Size: The particle size can be measured by various techniques known in the art. For example, particle size can be measured by sieve analysis or by a Camsizer® particle size and shape analysis system. While specifically described with respect to particulate or spherical shapes, the supported metal catalyst described herein can be in the form of extrudates, tablets or can be of irregular granular shape.

In the broadest sense, there is described a method for making a supported tantalum oxide catalyst precursor or catalyst with controlled Ta distribution. In an embodiment, the method comprises providing solid oxide or mixed oxide particles having a surface hydroxyl concentration. The solid oxide or mixed oxide particles may comprise ($SiO_2$), alumina ($Al_2O_3$), titania ($TiO_2$), zirconia ($ZrO_2$), hafnium oxide ($HfO_2$), magnesium oxide (MgO) or combinations thereof, as described herein.

The supported tantalum oxide catalysts described herein may be used, inter alia, in the production of 1,3-butadiene from ethanol and the decomposition of methyl t-butyl ether to isobutene and methanol. In many cases it is desirable to conduct these reactions in the packed-bed configuration for industrially relevant scales. Consequently, the supported tantalum oxide catalyst should have an equivalent particle diameter>0.5 mm (e.g. 1-5 mm) to operate the process at practically acceptable pressure drops across the reactor bed. Catalyst particles of this size can be in the form of a bead, granule or extrudate, with a bead being one of the more commonly used form. In one embodiment, the solid oxide or mixed oxide particles described herein may have an average diameter ranging from 0.5-5 mm, such as from 2-4 mm. The solid oxide or mixed oxide particles have an average surface area ranging from 200 to 600 $m^2/g$, such as 300 to 400 $m^2/g$. The solid oxide or mixed oxide particles may also have a pore volume ranging from 0.7 to 1.8 cc/g, such as 1.0 to 1.5 cc/g.

The methods described herein involve selecting a Ta-precursor material which reacts with the surface hydroxyl of the oxide support. For example, silica support without being exposed to treatment at temperatures>200° C. typically has a surface hydroxyl concentration of about 4.6 $OH/nm^2$. Using Ta-precursor in amounts such that the Ta to surface hydroxyl molar ratio (Ta:OH) is high will give a more uniform distribution of Ta in a catalyst precursor or catalyst particle as there will be sufficient Ta-precursor molecules to react with the available hydroxyls. For instance, a silica support with a surface area of 320 $m^2/g$ and hydroxyl concentration of 4.6 $OH/nm^2$ will have a weight-based Ta loading of 12.5% assuming that each Ta-precursor molecule reacts with three surface hydroxyls (Ta:OH of 1:3). Many industrial applications do not require a supported tantalum oxide catalyst with high Ta loading as high Ta loading may provide no added benefit, may even be detrimental to the catalytic performance, and is economically disadvantageous due to Ta cost. Indeed most industrial applications of supported tantalum oxide catalysts require 1 to 6 wt % Ta which correspond to a Ta:OH molar ratio of 0.02 to 0.15, for a silica with surface area 320 $m^2/g$ and hydroxyl concentration of 4.6 $OH/nm^2$. The embodiments discussed herein describe methods to control Ta distribution in a supported tantalum oxide catalyst precursor or catalyst at Ta levels substantially below the hydroxyl saturation level.

The molar Ta:OH ratio of a catalyst precursor or catalyst is calculated from the concentration of hydroxyl groups which are present in the support particles and the desired Ta content of the catalyst precursor or catalyst particles. The concentration of hydroxyl groups in the support particles can be quantitatively determined by thermogravimetric analysis (TGA) if the support is of high purity and contains only accessible surface hydroxyls or by titration methods, while the Ta content of the catalyst precursor or catalyst can be determined by the ICP method. Changes in the Ta:OH molar ratio can be affected by varying the Ta content in the catalyst precursor or catalyst, or controlling the concentration of hydroxyl groups in the support by methods described herein, or combination of both.

To achieve the desired target of Ta content in the catalyst precursor or catalyst, a specified amount of Ta-precursor is dissolved in an organic solvent. The specified amount of Ta-precursor is dependent on the preparation method and preparation conditions used. For example, when incipient impregnation method is used, the specified amount of Ta-precursor is the "theoretical amount" required, which is the amount calculated to achieve the target Ta content in the catalyst precursor or catalyst assuming 100% of the Ta-precursor is retained in the catalyst precursor or catalyst. However, when slurry reaction method is used, the specified amount of Ta-precursor is typically higher than the theoretical amount and is dependent on several factors including the reaction equilibrium constant and whether the Ta-impregnated particles are washed with an organic solvent to remove the un-reacted Ta-precursor from the support pores. The term 'equilibrium constant' used herein means the ratio of the amount of Ta-precursor that reacts with the hydroxyls to the amount of Ta-precursor used in the reaction solution when the reaction solution is in equilibrium with the support. The time required to reach such an equilibrium is the 'equilibrium time'. For example, if the equilibrium reaction constant is 0.7, if the reaction time is approaching equilibrium time, and if the Ta-impregnated particles are washed to remove the un-reacted Ta-precursors, the specified amount of tantalum precursor to be added is the theoretical amount divided by the equilibrium constant, in this case, 0.7. Those skilled in the art will appreciate that the equilibrium constant and equilibrium time will not only vary with the Ta-precursor used, but also with other parameters which can influence a chemical reaction like reaction temperature, type of oxide support, type of solvent, presence of other chemical modifiers (described below), etc.

The method described herein comprises selecting a Ta-precursor material having a reaction rate (or "reactivity") that will provide a desired Ta distribution in the resulting catalyst precursor or catalyst particle. For example, in an embodiment, the selected Ta-precursor material has a reaction rate with the solid oxide or mixed oxide particles that is faster than the mass transfer rate of the precursor towards the center of the particle. In this embodiment, the resulting catalyst precursor or catalyst particles have an egg-shell distribution of Ta with the concentration of Ta being greater toward the exterior surface of the particles than on inside, as defined herein. In this embodiment, the Ta loading is below the level required to consume all available hydroxyl groups, or at low Ta:OH ratios.

In another embodiment, the selected Ta-precursor material has a reaction rate with solid oxide or mixed oxide particles that is approximate to or slower than the mass transfer rate of the precursor towards the center of the particle. In this embodiment, the resulting catalyst precursor or catalyst particles have a uniform distribution of Ta throughout the particle even when the Ta:OH ratio is low. As used herein, a "low ratio" means substantially below the ratio for saturation, which is 1:3 (i.e. 0.33) assuming every Ta reacts with 3 hydroxyls. For example, the Ta:OH may be below 0.15.

As used herein, the reaction rate or reactivity of the Ta-precursor refers to the rate at which a particular precursor reacts with hydroxyl groups. This rate is typically determined by the number, size, and complexity of the functional groups attached to the Ta-precursor. In general, as the size and complexity of the functional groups increase, the reactivity decreases.

Non-limiting examples of Ta-precursors that may be used herein include Ta-tetraethoxide-2,4-pentanedionate for more uniform Ta distribution or Ta-ethoxide for more egg-shell Ta distribution. One may also change the reactivity of a Ta-precursor by adding at least one chemical modifier, such as a stabilizer. For example, one can reduce the reactivity of Ta-ethoxide with surface hydroxyls by in-situ addition of 2,4-pentanedione (acetyl acetone) to the impregnation solution. 2,4-pentanedione forms a complex with Ta-ethoxide, and the resultant complex has a lower rate of reaction with surface hydroxyls than Ta-ethoxide alone. Additionally, one can tune the reactivity of Ta-ethoxide with the hydroxyls by altering the molar ratio of 2,4-pentanedione to Ta-ethoxide. Furthermore, one may also influence the reactivity of the Ta-precursor with the hydroxyl groups by varying the solvent used. For example, when using Ta-ethoxide stabilized by 2,4-pentanedione as stabilizer, the Ta-precursor reaction rate with hydroxyls is faster when using methanol than when using 2-propanol.

The method further comprises contacting the solid oxide or mixed oxide particles with Ta-precursor material to form Ta-impregnated particles. For example, in an embodiment, the contacting step comprises adding the organic solution comprising the Ta-precursor material to the solid oxide or mixed oxide particles via incipient wetness impregnation or slurry reaction. In an embodiment, the Ta-precursor is mixed with an organic solvent to form a solution. A sufficient amount of the solution can then be added to the formed support particles to only fill the pores of the formed particles. In this incipient wetness impregnation method, there is substantially no free solvent in the samples. In the slurry reaction method, the volume of the solution formed after mixing the Ta-precursor with an organic solvent is substantially more than the volume available in the pores of the formed particles. Therefore, the system comprising the formed particles and the solution forms a slurry.

The method described herein further includes recovering the Ta-impregnated solid oxide support to form catalyst precursor particles with a desired Ta distribution, as described herein. For example, this step comprises removal of solvent, such as by evaporation. In one embodiment, recovering the particles having tantalum impregnated in a solid oxide, such as a silica gel, involves separating the formed silica gel particles from the organic solvent by conventional means, and optionally washing the particles with a solvent. This may involve draining the organic solvent from the formed silica gel particles and then drying the formed silica gel particles. Drying, which could include vacuum drying, involves bringing the formed silica gel particles to the boiling point of the organic solvent. The drying conditions may vary but are carried out until nearly all of the organic solvent has evaporated. For both slurry reaction and incipient wetness impregnation techniques, contact time between the Ta bearing solution and the solid oxide support should not be substantially shorter than the equilibrium time. If the contact time is much shorter than the equilibrium time for the slurry reaction technique, the amount of Ta reacted with the hydroxyls may be substantially lower than the amount that should have been reacted according to the equilibrium constant, and final Ta concentration in the catalyst may be less than target. If the contact time is much shorter than the equilibrium time for incipient wetness impregnation technique, during the solvent evaporation step the unreacted Ta-precursor may migrate towards the surface of the solid oxide possibly leading to a more non-uniform Ta distribution that may not be desired.

The method may further comprise of optionally calcining the catalyst precursor particles at a temperature of at least 400° C. to oxidize the Ta-complex in the catalyst precursor to form supported tantalum oxide catalyst particles.

In an embodiment, one can also control the number (or concentration) of surface hydroxyls available to react with the Ta-precursor to obtain the desired Ta distribution on an oxide support. As described above, at low Ta:OH ratios, if the selected Ta-precursor material has a reaction rate with the solid oxide or mixed oxide particles that is faster than the mass transfer rate of the precursor towards the center of the particle, the resulting catalyst will have an egg-shell distribution. However, if the number of surface hydroxyls available to react with the same Ta-precursor at similar Ta loadings is reduced before the oxide support and Ta-precursor are mixed, the Ta:OH ratio will increase and the catalyst particle will have intermediate or uniform Ta distribution depending on the extent of reduction of the surface hydroxyl groups. This is because the Ta-precursor will have to diffuse deeper into the particle to seek unreacted surface hydroxyls to react with. The number of surface hydroxyl groups can be reduced by thermal treatment, e.g. calcination.

In one embodiment, the method of controlling Ta distribution in a supported tantalum oxide catalyst is achieved by controlling the hydroxyl content in the silica support via thermal treatment of the support. An example of the effects of temperature on the dehydroxylation of a silica surface is shown in L. T. Zhuravlev, The surface chemistry of amorphous silica. Zhuravlev model, Colloids and Surfaces A: Physicochem. Eng. Aspects 173 (2000) 1-38, specifically at FIG. 9 and its corresponding description, all of which is herein incorporated by reference. It demonstrates that the silica hydroxyl concentration decreases with increasing treatment temperature.

In an embodiment, the method described herein may comprise calcining the solid oxide or mixed oxide particles for a time and at a temperature sufficient to reduce the hydroxyl concentration to the desired level. For example, when the solid oxide comprises silica, the hydroxyl comprises silanol groups, and calcining of the silica is performed at a temperature of at least 200° C. to form siloxane groups from the condensation of the silanol groups.

There is also provided herein a supported tantalum oxide catalyst precursor or catalyst with controlled Ta distribution made by the method described herein. For example, in an embodiment, the supported tantalum oxide catalyst precursor or catalyst described herein has a controlled Ta distribution which has an egg-shell distribution of Ta with the concentration of Ta being greater near the exterior surface of the particle than on inside. In another embodiment, the controlled Ta distribution comprises a uniform distribution of Ta throughout the particle.

In an embodiment, the supported Ta catalyst described herein has a Ta concentration ranging from 0.1-0.6 $Ta/nm^2$, or 1-6 wt % if the support has a surface area of 320 $m^2/g$.

In one embodiment, there is described a supported metal catalyst having a uniform distribution of Ta and a desired tantalum:hydroxyl molar ratio (i.e. Ta:OH) that is below the OH-saturation level. For example, at 3.0 wt % Ta (i.e., ~3.6 wt % $Ta_2O_5$) loading on a 320 $m^2/g$ silica support, the Ta:OH is 0.07:1 (assuming OH density of 4.6 $OH/nm^2$), which is well below OH-saturation level of 0.33:1 assuming that each Ta-precursor molecule reacts with 3 surface hydroxyl groups.

In one embodiment, there is disclosed a method of controlling Ta distribution of the catalyst precursor or catalyst using a combination of methods described herein. For example, in one embodiment, there is disclosed a method of controlling Ta distribution in a supported tantalum oxide catalyst precursor or catalyst by using the disclosed thermal method to control the concentration of available surface hydroxyls on the support, while also controlling Ta-precursor reactivity. In one embodiment, the disclosed thermal method comprises pre-calcining the support.

There is also disclosed the use of the catalyst described herein for the conversion of a feed comprising at least ethanol into butadiene. For example, literature describes the use of a supported tantalum oxide catalyst (with 2 wt %

Ta$_2$O$_5$) for the conversion of a feed containing at least ethanol to butadiene at a temperature in the range between 300° C. and 400° C., at a pressure ranging from 0.1 to 1.0 MPa, and a liquid hourly space velocity in the range 0.2 to 2.0. See, e.g., Corson, B. B.; Stahly, E. E.; Jones, H. E.; Bishop, H. D. *Industrial and Engineering Chemistry*, 41, 1012-1017 (1949), which is herein incorporated by reference for its teachings related to the conversion of a feed comprising ethanol into butadiene.

In one embodiment, there is disclosed a method for making a supported tantalum oxide catalyst precursor with controlled Ta distribution, the method comprising: providing a support comprising solid oxide or mixed oxide particles having a hydroxyl concentration; selecting a Ta-precursor material having a reactivity that will provide a desired Ta distribution in the resulting tantalum oxide catalyst particles; contacting the solid oxide or mixed oxide particles with an organic solution comprising the Ta-precursor material to form Ta-impregnated particles; and recovering the Ta-impregnated particles to form a catalyst precursor comprising a desired Ta distribution.

In one embodiment, the method may further comprise calcining the catalyst precursor to form a supported tantalum oxide catalyst comprising a desired Ta distribution.

As described herein, the selected Ta-precursor material has a reaction rate with the solid oxide or mixed oxide particles that is faster than the mass transfer rate of the precursor towards the center of the particle. This leads to catalyst precursor particles that have an egg-shell distribution of Ta.

In another embodiment, the selected Ta-precursor material has a reaction rate with solid oxide or mixed oxide particles that is approximate to or slower than the mass transfer rate of the precursor towards the center of the particle. This leads to catalyst precursor particles having a uniform distribution of Ta throughout the particle.

In one embodiment, the resulting catalyst precursor particles have a Ta:OH ratio that is below the OH-saturation level, such as a Ta:OH ratio is less than 0.15.

In one embodiment, the solid oxide or mixed oxide support comprises silica (SiO$_2$), alumina (Al$_2$O$_3$), titania (TiO$_2$), zirconia (ZrO$_2$), hafnium oxide (HfO$_2$), magnesium oxide (MgO), silica-alumina, silica-zirconia, silica-titania, or combinations thereof. The solid oxide or mixed oxide particles have less than 5 wt % moisture.

In one embodiment, the solid oxide or mixed oxide particles have an average diameter ranging from 0.5 to 5 mm.

In one embodiment, the solid oxide or mixed oxide particles may also have a surface area ranging from 200 to 600 m$^2$/g and/or a pore volume ranging from 0.7 to 1.8 cc/g.

In one embodiment, the contacting step described herein comprises adding the organic solution comprising the Ta-precursor material to the solid oxide or mixed oxide particles via incipient wetness impregnation or slurry reaction.

In one embodiment, recovering the Ta-impregnated particles includes removing solvent that has been mixed with the Ta-precursor material.

In one embodiment, the Ta-precursor comprises Ta-tetra-ethoxide-2,4-pentanedionate, Ta-ethoxide, or a combination of Ta-ethoxide and 2,4-pentanedione (acetyl acetone).

In one embodiment, at least a chemical process to stabilize a Ta-precursor with a modifier in order to control the rate of reaction between the Ta-precursor and the support material is used.

In one embodiment, there is described a method for making a supported tantalum oxide catalyst precursor with controlled Ta distribution, the method comprising: providing a support comprising solid oxide or mixed oxide particles having hydroxyl groups attached thereto; selecting a Ta-precursor material that has a desired reaction rate with the hydroxyl groups; controlling the number of hydroxyl groups to react with the Ta-precursor by at least one thermal process; contacting the solid oxide or mixed oxide particles having the controlled number of the hydroxyl groups with the Ta-precursor material to form Ta-impregnated particles; and recovering the Ta-impregnated particles to form a catalyst precursor comprising a desired Ta distribution.

In an embodiment, the described method may further comprise calcining the catalyst precursor to form a supported tantalum oxide catalyst comprising a desired Ta distribution.

In one embodiment, the catalyst precursor or catalyst is in the form of a bead, granule or extrudate.

In an embodiment, there is further described a supported tantalum oxide catalyst precursor with a controlled Ta distribution, made using the disclosed method. For example, the method comprises providing a support comprising solid oxide or mixed oxide particles having a hydroxyl concentration; selecting a Ta-precursor material having a reactivity that will provide a desired Ta distribution in the resulting tantalum oxide catalyst particles; contacting the solid oxide or mixed oxide particles with an organic solution comprising the Ta-precursor material to form Ta-impregnated particles; recovering the Ta-impregnated particles to form a catalyst precursor comprising a desired Ta distribution. In an embodiment, the method further comprises calcining the catalyst precursor to form a supported tantalum oxide catalyst comprising a desired Ta distribution.

In an embodiment, there is further described a supported tantalum oxide catalyst precursor with a controlled Ta distribution, made using the disclosed method. For example, the method comprises providing a support comprising solid oxide or mixed oxide particles having hydroxyl groups attached thereto; selecting a Ta-precursor material that has a desired reaction rate with the hydroxyl groups; controlling the number of hydroxyl groups to react with the Ta-precursor by at least one thermal process; contacting the solid oxide or mixed oxide particles having the controlled number of the hydroxyl groups with an organic solution comprising the Ta-precursor material to form Ta-impregnated particles; and recovering the Ta-impregnated particles to form a catalyst precursor comprising a desired Ta distribution. In an embodiment, the method further comprises calcining the catalyst precursor to form a supported tantalum oxide catalyst comprising a desired Ta distribution.

In an embodiment, there is further described a method for producing butadiene from ethanol. For example, the method comprises contacting ethanol with a supported tantalum oxide catalyst made using a method comprising: providing a support comprising solid oxide or mixed oxide particles having a hydroxyl concentration; selecting a Ta-precursor material having a reactivity that will provide a desired Ta distribution in the resulting tantalum oxide catalyst particles; contacting the solid oxide or mixed oxide particles with an organic solution comprising the Ta-precursor material to form Ta-impregnated particles; recovering the Ta-impregnated particles to form a catalyst precursor comprising a desired Ta distribution. In an embodiment, the method further comprises calcining the catalyst precursor to form a supported tantalum oxide catalyst comprising a desired Ta distribution.

In an embodiment, there is further described a method for producing butadiene from ethanol. For example, the method comprises contacting ethanol with a supported tantalum oxide catalyst made using a method, which comprises providing a support comprising solid oxide or mixed oxide particles having hydroxyl groups attached thereto; selecting a Ta-precursor material that has a desired reaction rate with the hydroxyl groups; controlling the number of hydroxyl groups to react with the Ta-precursor by at least one thermal process; contacting the solid oxide or mixed oxide particles having the controlled number of the hydroxyl groups with an organic solution comprising the Ta-precursor material to form Ta-impregnated particles; and recovering the Ta-impregnated particles to form a catalyst precursor comprising a desired Ta distribution. In an embodiment, the method further comprises calcining the catalyst precursor to form a supported tantalum oxide catalyst comprising a desired Ta distribution.

The features and advantages of the catalysts and methods disclosed herein are illustrated by the following examples, which are not to be construed as limiting the scope of the present disclosure in any way.

EXAMPLES

In all the following examples, the support used is a silica gel bead with following typical properties: a size ranging from 2-5 mm; a surface area of approximately 320 $m^2/g$, a pore volume of approximately 1.05 cc/g; and an average pore diameter of approximately 131 Å. In all cases the silica gel was pre-dried to a loss of drying (LOD)<0.5 wt %, measured at 120° C., before use.

Silica Support Fabrication

Figure 1:
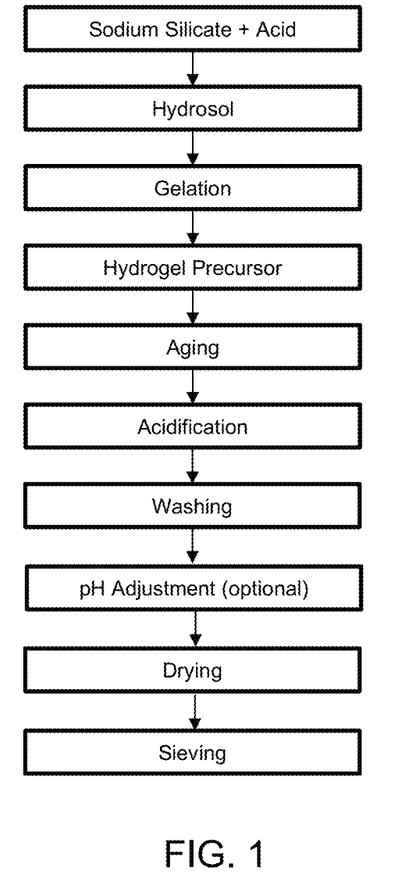
FIG. 1 is a flow chart showing the general steps used in making silica support according to an embodiment of the present disclosure.

In one embodiment, the support comprises silica. The following is a description of the general steps used for making the silica support according to an embodiment of the present disclosure. A flow chart showing the general steps used in making silica support according to an embodiment of the present disclosure is provided in FIG. 1. A more detailed description of the silica support and methods of making it are found in co-pending application Ser. No. 16/804,610, which is herein incorporated by reference.

In one embodiment, a dilute sodium silicate solution of 3.3 weight ratio $SiO_2:Na_2O$ was first reacted with dilute sulfuric acid to form a hydrosol having the following composition: 12 wt % $SiO_2$ and $H_2SO_4:Na_2O$ in a molar ratio of 0.8. As a result, the resulting hydrosol was basic. In one embodiment, the sodium silicate solution contained approximately 400 ppm Al on $SiO_2$ weight basis. In one embodiment, a higher purity silicate with low Al can be used to make silica with lower Al content.

The hydrosol was then sprayed into air, where it broke into droplets and solidified into beads having a diameter of several millimeters before it was caught in a solution such as water or a solution that buffers the pH of the beads/solution system at a basic pH of ~9 (such as aqueous solution of ammonium sulfate, sodium bicarbonate, etc.). Aging was conducted at 70° C. for about 16 hours to achieve a gel having a surface area of about 300 $m^2/g$.

Acid was then added to lower the pH to ~2. The beads were then washed with water that was acidified to a pH ~3 to reduce Na levels. Once washed, the pH of the beads was increased to ~9 using ammonium hydroxide solution. The beads were then dried using an oven. Finally, the beads were sieved to get the desired particle size fraction. Note that pH adjustment before drying is optional, and beads are typically dried from pH 3-9.

In one embodiment, the described process can be modified to optionally include multiple aging steps at increasing temperatures with each aging step followed by acidification and washing steps to get the desired combination of surface area and Na levels.

Using the above procedure one can get a silica gel bead with a surface area~300 $m^2/g$, pore volume~1.0 cc/g, Al<500 ppm (depending on silicate purity), Na<1000 ppm (depending on extent of washing in combination with multiple aging steps).

Example 1: Egg-shell Distribution

A solution was made by dissolving 1.77 g Ta-ethoxide in 24.2 g 2-propanol. This solution was then quickly impregnated on 30 g of pre-dried silica gel beads. Impregnation took less than 15 minutes. The impregnated silica gel was kept in a sealed container for at least 1 hour before evaporating the solvent using an explosion-proof hot-plate. The dried material was then calcined up to 500° C. for 4 hours in air to give the finished catalyst, which had 2.4 wt % Ta.

Example 2: Uniform Distribution with Ta-tetraethoxide-2,4,-pentanedionate

A solution was made by dissolving 4.88 g of Ta-tetraethoxide-2,4,-pentanedionate (CAS#20219-33-4) in 60 g 2-propanol. This solution was then quickly impregnated on 75 g of pre-dried silica gel beads. Impregnation took less than 15 minutes. The impregnated silica gel was kept in a sealed container for at least 1 hour before evaporating the solvent using an explosion proof hot-plate. The dried material was then calcined up to 500° C. for 4 hours air to give the finished catalyst, which had 2.2 wt % Ta.

Example 3: Uniform Distribution with Ta-Ethoxide+Acetyl Acetone

A stabilized Ta-precursor solution was made by mixing 10 g Ta-ethoxide with 4.95 g of 2,4-pentanedione (acetyl acetone). 6.8 g of the stabilized Ta-precursor solution was dissolved in 60 g isopropanol, which was then quickly impregnated on 80 g of pre-dried silica gel beads. Impregnation took less than 15 minutes. The impregnated silica gel was kept in a sealed container for at least 1 hour before evaporating the solvent using an explosion proof hot-plate. The dried material was then calcined up to 500° C. for 4 hours in air to give the finished catalyst, which had 2.5 wt % Ta.

Figure 2:
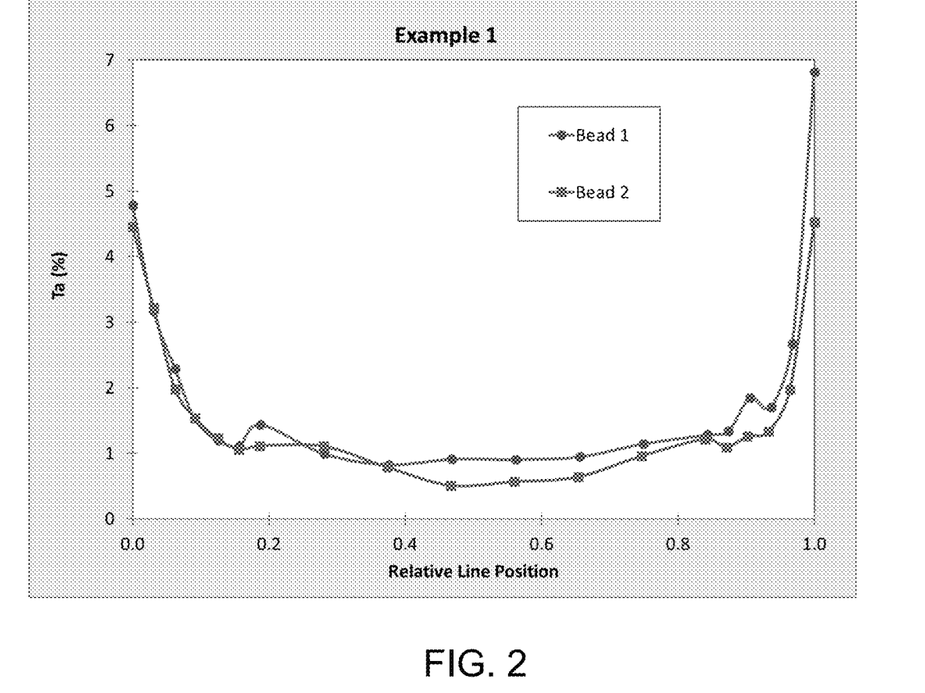
FIG. 2 is a line graph of Ta distribution data for samples made according to Example 1.
Figure 3:
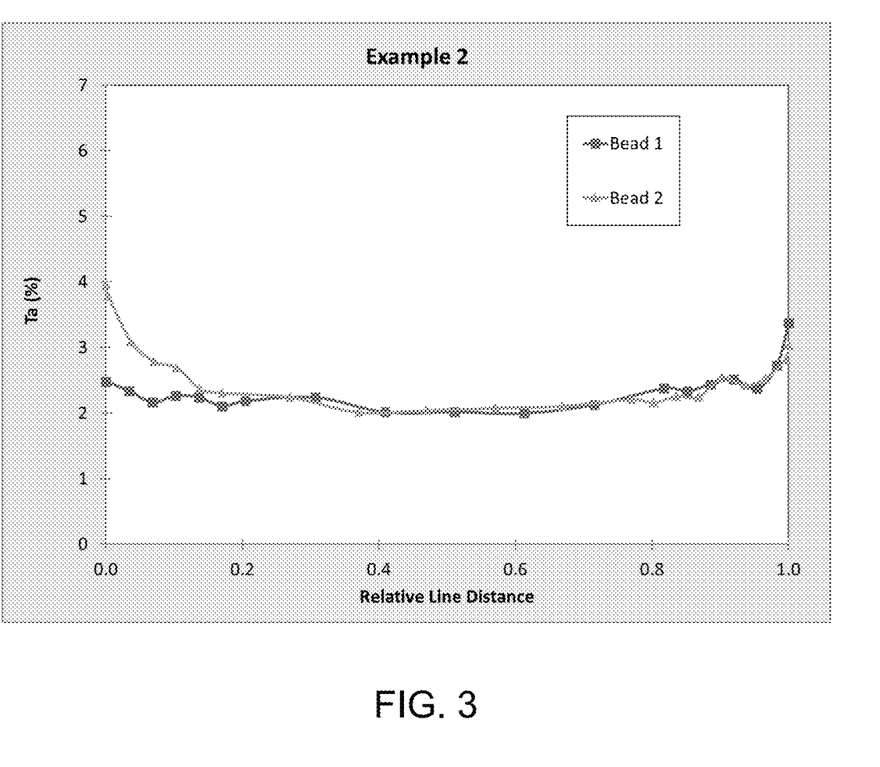
FIG. 3 is a line graph of Ta distribution data for samples made according to Example 2.
Figure 4:
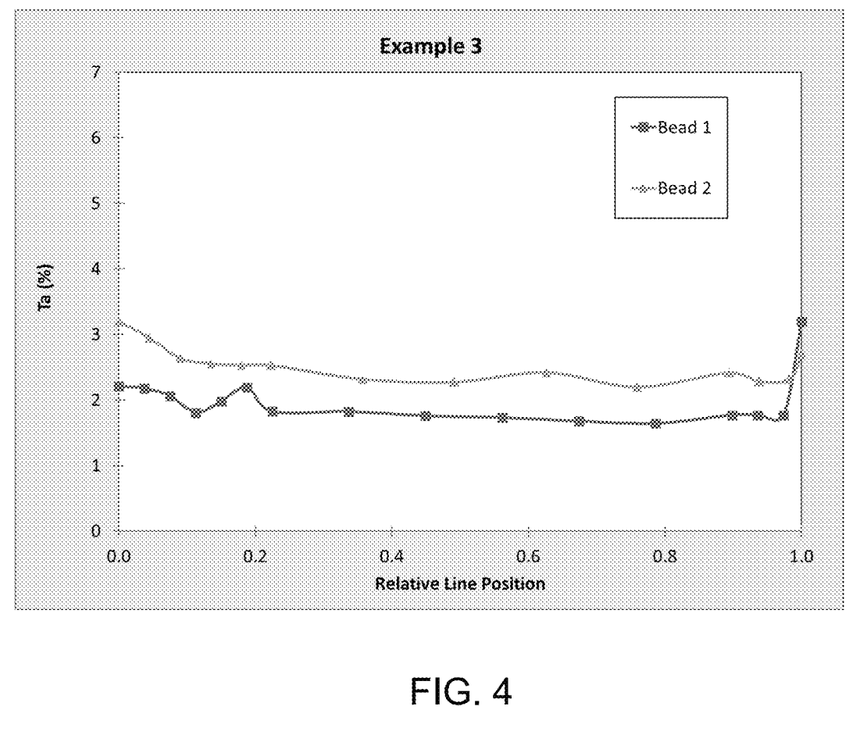
FIG. 4 is a line graph of Ta distribution data for samples made according to Example 3.

As described above, the product from Example 1 exhibited an egg-shell type of Ta distribution with most Ta concentrated towards the surface of the beads due to the faster reaction rate of Ta-ethoxide with silica silanols than the mass transfer rate of the precursor towards the center of the bead. In contrast, when Ta-tetraethoxide-2,4,-pentanedionate was used, as in Example 2, a more uniform Ta distribution throughout the bead was achieved. A similar result to Example 2 was achieved when a 2:1 molar mixture of acetyl acetone: Ta-ethoxide was used, as shown in Example 3. Ta-precursors used in Examples 2 and 3 had lower reaction rate with the silica silanols, allowing the precursor to diffuse through the bead before the reaction was complete, leading to a more uniform Ta distribution. The above examples demonstrate that one can control Ta-distribution in a catalyst by tuning the Ta-precursor reaction rate with the support material (here silica) compared to its mass transfer rate by selecting an appropriate precursor, or by in-situ chemical modification of the precursor.

The results of Examples 1-3 are graphically depicted in FIGS. 2-4. These figures show that by choosing a Ta-precursor with desired reaction rate, either uniform or egg-shell distribution can be achieved at low Ta:OH ratio consistent with the present description. For example, Example 1 uses a fast-reacting Ta-precursor to achieve an eggshell distribution. On the other hand, Examples 2 and 3 use a complex, slow reacting Ta-precursor to achieve a uniform Ta distribution. In all examples, the Ta:OH molar ratio is approximately 0.06:1.

Example 4: Influence of Modifier on Ta Reaction Rate

In this series of experiments, for each sample around 30 g of silica gel was mixed with a solution of Ta-ethoxide (TE, ~1.73 g) with or without 2,4-pentanedione (AcAc, 0.83 g) dissolved in ~70 g 2-propanol solvent. The total solution amount was ~3 times the available pore volume in the silica beads, and therefore these samples were prepared using the "slurry reaction" technique described above. The mixture was allowed to mix on an oscillating shaker for the time listed in Table 1. Then, the excess solution was drained (decanted), and the beads were dried on an explosion proof hot plate to evaporate the solvent retained in the pores. The dried beads were calcined at 550° C. for 4 hours. Ta was measured using ICP in the spent-reaction solution and the calcined beads to determine extent of reaction of the Ta-precursor with the silica gel beads. Results are listed in Table 1. EDS lines scans were also measured on the samples to evaluate Ta-distribution through the bead.

Figure 5A:
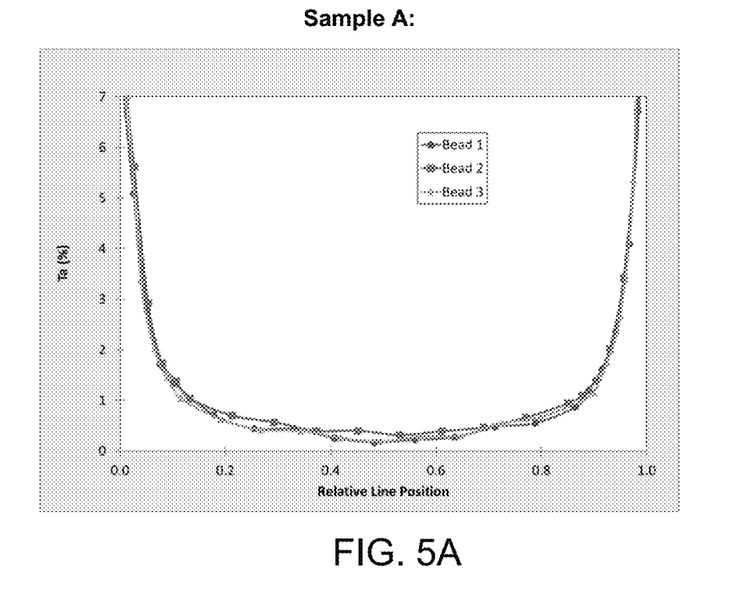
FIGS. 5A-5C are line graphs of Ta distribution data for samples made according to Example 4, showing the influence of modifier on Ta reaction rate for samples A, B and C, respectively.
Figure 5B:
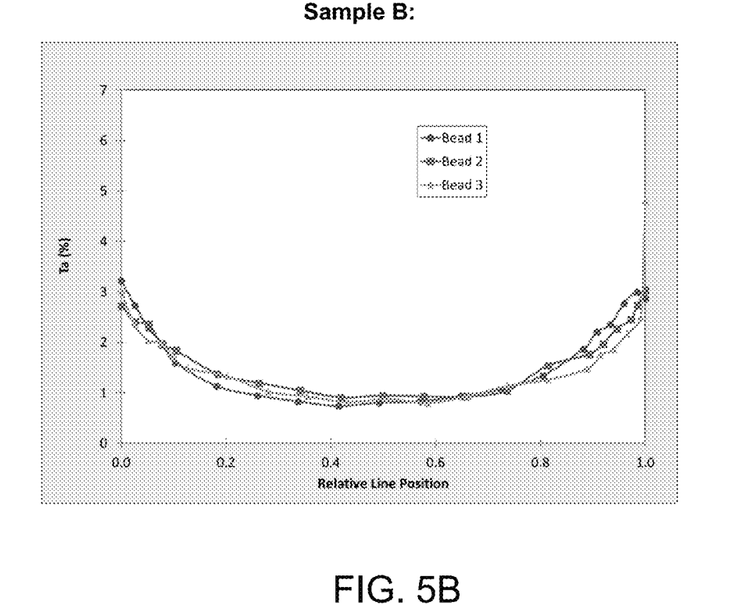

Comparing samples A and B, it is seen that when 2,4-pentanedione (AcAc) is added with the Ta-ethoxide for similar contact time (1.5 hours), much less Ta remains on the silica compared to when Ta-ethoxide is used without any modifier. This suggests that presence of 2,4-pentanedione slows down the reaction of Ta-ethoxide with silica. Also, sample A has an egg-shell Ta distribution, while sample B has a more uniform Ta distribution than sample A.

Figure 5C:
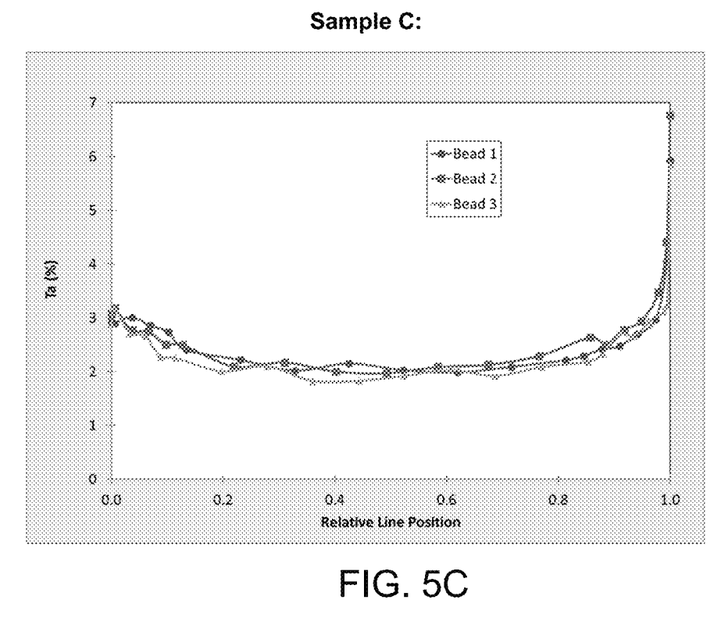

Comparing samples B and C, it is seen that with increasing contact time, more Ta reacts with the silica.

Comparing Ta-distribution for samples A and C, we see that sample A has an egg-shell Ta distribution, while sample C has a uniform Ta distribution.

TABLE 1

| Sample | Ta-precursor | Contact Time (hr) | Ta in silica (wt %) | Ta in solution (wt %) |
|---|---|---|---|---|
| A | TE | 1.5 | 2.41 | 0.1 |
| B | TE + AcAc | 1.5 | 1.69 | 0.53 |
| C | TE + AcAc | 24 | 2.06 | 0.26 |

Example 5: Influence of Solvent

Table 2 summarizes data for slurry reactions between silica gel beads and solutions containing Ta-ethoxide in the presence of 2,4-pentanedione (acetylacetone, AcAc) using various ratios of methanol (MeOH) and 2-propanol (IPA) as solvent. Experimental procedure and processing conditions were similar to Example 4, except where noted. Data shows that increasing amounts of methanol in the solvent mixture leads to faster reaction of the Ta-precursor with silica support (i.e. surface hydroxyls). Literature on hydrolysis of metal-alkoxides suggests that hydrolysis is influenced by steric factors among other things. Increase in alkyl chain length or branching slows down hydrolysis. Once the Ta-ethoxide, 2,4-pentanedione and solvent molecules are mixed, the acetylacetonate and alkoxy (i.e. methoxy, ethoxy, 2-propoxy) ligands are expected to be in dynamic equilibrium around the $Ta^{+5}$ ion. Therefore, as methanol content in the solution increases the probability of $Ta^{+5}$ coordinated with methoxy groups increases, thereby increasing the reaction rate of Ta-precursor with silanols.

TABLE 2

| Sample | Ta-precursor | Solvent | Methanol:2-Propanol Molar Ratio | Contact Time (hr) | Ta in silica (wt %) | Ta in solution (wt %) |
|---|---|---|---|---|---|---|
| D | TE + AcAc | MeOH | ∞ | 1.5 | 2.39 | 0.05 |
| E | TE + AcAc | MeOH + IPA | 1.88 | 1.5 | 2.24 | 0.15 |
| F | TE + AcAc | MeOH + IPA | 1.0 | 1.5 | 2.33 | 0.15 |
| G | TE + AcAc | MeOH + IPA | 0.2 | 1.5 | 2.00 | 0.36 |
| H | TE + AcAc | IPA | 0 | 1.5 | 1.69 | 0.53 |

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure.

Other embodiments of the catalysts and methods of the present disclosure will be apparent to those skilled in the art from consideration of the specification and practice of the embodiments disclosed herein. It is intended that the specification and examples be considered as exemplary only, with the true scope of this application being indicated by the following claims.

What is claimed is:

1. A method for making a supported tantalum oxide catalyst precursor with controlled Ta distribution, the method comprising:
   providing a support comprising solid oxide or mixed oxide particles having a hydroxyl concentration;
   selecting a Ta-precursor material having a reactivity that will provide a desired Ta distribution in the resulting tantalum oxide catalyst precursor particles;
   contacting the solid oxide or mixed oxide particles with an organic solution containing the Ta-precursor material to form Ta-impregnated particles; and
   recovering the Ta-impregnated particles to form a catalyst precursor comprising a desired Ta distribution, wherein the method further comprises at least a chemical process to stabilize the Ta-precursor with at least one modifier in order to control the rate of reaction between the Ta-precursor and the support material.

2. The method of claim 1, further comprising calcining the catalyst precursor to form a supported tantalum oxide catalyst comprising a desired Ta distribution.

3. The method of claim 1, wherein the selected Ta-precursor material has a reaction rate with the solid oxide or mixed oxide particles that is faster than the mass transfer rate of the precursor towards the center of the particle.

4. The method of claim 3, wherein the resulting catalyst precursor particles have an egg-shell distribution of Ta.

5. The method of claim 1, wherein the selected Ta-precursor material has a reaction rate with solid oxide or mixed oxide particles that is approximate to or slower than the mass transfer rate of the precursor towards the center of the particle.

6. The method of claim 5, wherein the resulting catalyst precursor particles have a uniform distribution of Ta throughout the particle.

7. The method of claim 1, wherein the resulting catalyst precursor particles have a Ta:OH ratio that is below the OH-saturation level.

8. The method of claim 7, wherein the Ta:OH ratio is less than 0.15.

9. The method of claim 1, wherein the solid oxide or mixed oxide support comprises silica ($SiO_2$), alumina ($Al_2O_3$), titania ($TiO_2$), zirconia ($ZrO_2$), hafnium oxide ($HfO_2$), magnesium oxide (MgO), silica-alumina, silica-zirconia, silica-titania, or combinations thereof.

10. The method of claim 9, wherein solid oxide or mixed oxide particles have less than 5 wt % moisture.

11. The method of claim 9, wherein the solid oxide or mixed oxide particles have an average diameter ranging from 0.5 to 5 mm.

12. The method of claim 9, wherein the solid oxide or mixed oxide particles have an average surface area ranging from 200 to 600 $m^2/g$.

13. The method of claim 9, wherein the solid oxide or mixed oxide particles have an average pore volume ranging from 0.7 to 1.8 cc/g.

14. The method of claim 1, wherein said contacting comprises adding the organic solution comprising the Ta-precursor material to the solid oxide or mixed oxide particles via incipient wetness impregnation or slurry reaction.

15. The method of claim 1, wherein recovering the Ta-impregnated particles includes removing solvent that has been mixed with the Ta-precursor material.

16. The method of claim 1, wherein said Ta-precursor comprises Ta-tetraethoxide-2,4-pentanedionate, Ta-ethoxide, or a combination of Ta-ethoxide and 2,4-pentanedione (acetyl acetone).

17. The method of claim 1, wherein the Ta-precursor comprises Ta-ethoxide.

18. The method of claim 1, wherein the modifier for the Ta-precursor comprises 2,4-pentanedione.

19. The method in claim 1, wherein the Ta-precursor is Ta-ethoxide and the modifier is 2,4-pentanedione.

20. A method for making a supported tantalum oxide catalyst precursor with controlled Ta distribution, the method comprising:
providing a support comprising solid oxide or mixed oxide particles having hydroxyl groups attached thereto;
selecting a Ta-precursor material that has a desired reaction rate with said hydroxyl groups;
controlling the number of hydroxyl groups to react with said Ta-precursor by at least one thermal process;
contacting the solid oxide or mixed oxide particles having the controlled number of the hydroxyl groups with an organic solution comprising the Ta-precursor material to form Ta-impregnated particles; and
recovering the Ta-impregnated particles to form a catalyst precursor comprising a desired Ta distribution,
wherein the method further comprises at least a chemical process to stabilize the Ta-precursor with at least one modifier in order to control the rate of reaction between the Ta-precursor and the support material.

21. The method of claim 20, further comprising calcining the catalyst precursor to form a supported tantalum oxide catalyst comprising a desired Ta distribution.

22. The method of claim 20, wherein the thermal process comprises calcining the support to reduce the hydroxyl concentration thereon.

* * * * *